US008623367B2

(12) United States Patent
Momm et al.

(10) Patent No.: US 8,623,367 B2
(45) Date of Patent: Jan. 7, 2014

(54) ANTIBODY FORMULATION (75) Inventors: Joachim Momm, Freiburg (DE); Hans-Joachim Wallny, Grenzach-Wyhlen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/586,185

(22) Filed: Aug. 15, 2012

(65) Prior Publication Data
US 2012/0315285 A1 Dec. 13, 2012

Related U.S. Application Data (63) Continuation of application No. 13/133,843, filed as application No. PCT/EP2009/066675 on Dec. 9, 2009.

(30) Foreign Application Priority Data

Dec. 10, 2008 (EP) .................................... 08170884

(51) Int. Cl.
A61K 39/395 (2006.01)
C07K 16/24 (2006.01)

(52) U.S. Cl.
USPC ................. 424/145.1; 424/158.1; 530/388.23

(58) Field of Classification Search
None
See application file for complete search history.

(56) References Cited

U.S. PATENT DOCUMENTS

| 6,171,586 B1 | 1/2001 | Lam et al. | |
|---|---|---|---|
| 7,446,175 B2 | 11/2008 | Gram et al. | |
| 7,491,516 B2 * | 2/2009 | Collinson et al. | .......... 435/70.21 |
| 2003/0138417 A1 | 7/2003 | Kaisheva et al. | |
| 2008/0286266 A1 | 11/2008 | Lowe et al. | |

FOREIGN PATENT DOCUMENTS

| CN | 201044845 | 4/2008 |
|---|---|---|
| WO | WO 96/23067 | 8/1996 |
| WO | WO 97/04801 | 2/1997 |
| WO | WO 00/45818 | 8/2000 |
| WO | WO 01/21602 | 3/2001 |
| WO | WO 02/02773 | 1/2002 |
| WO | WO 02/16436 A | 2/2002 |
| WO | WO 03/039485 | 5/2003 |
| WO | 03105894 | 12/2003 |
| WO | WO2010100179 | 9/2010 |
| WO | WO2012028683 | 3/2012 |

OTHER PUBLICATIONS

Wang, Wei, "Instability, stabilization, and formulation of liquid protein pharmaceuticals", International Journal of Pharmaceuticals, vol. 185, pp. 129-188, (1999).
Cleland et al., "The Development of Stable Protein Formulations: A Close Look at Protein Aggregation, Deamidation, and Oxidation", Critical Reviews in Therapeutic Drug Carrier Systems, vol. 10(4), pp. 307-377, (1993).
Rieke et al., "The human ant-IL-11 monoclonal antibody ACZ885 is effective in joint inflammation models in mice and in a proof-of-concept study in patients with rheumatoid arthritis", Arthritis Research and Therapy, Biomed Central, London, GB, vol. 10, No. 3, pp. R67, Jun. 5, 2008.
Daugherty et al.,"Formulation and delivery issues for monoclonal antibody therapeutics", Adv. Drug Deliv. Rev., Aug. 7, 2006;58(5-6), pp. 686-706. Epub May 22, 2006.
Correa, Carlos, "Guidelines for the Examination of Pharmaceutical patents: Developing a Public Health Perspective", United Nations Conference on Trade & Development WHO pp. 6-8, Jan. 2007.
International Nonproprietary Names for Pharmaceutical Substances (INN): Proposed INN: List 97, WHO Drug Information 21(2):40, (2007).
"WHO International Nonproprietary Names Programme: canakinumab (87)", dated Feb. 2, 2007.
Sellers and Maa, "Principles of Biopharmaceutical Protein Formulation" from: Methods in Molecular Biology, vol. 308: Therapeutic Proteins: Methods and Protocols; Ed. Smales and James, Humana Press Inc., Totowa, NJ, (2005).
Narasimhan et al. "High-dose monoclonal antibodies vis the subcutaneous route: challenges and technical solutions, an industry perspective", Therapeutic Delivery, 3:889-900, (2012).
Lowe et al. "Aggregation, Stability, and Formulation of Human Antibody Therapeutics", Adv. Protein Chem. Struct. Biol., 84:41-61, (2011).
Krishnan et al. "Development of Formulations for Therapeutic Monoclonal Antibodies and Fc Fusion Proteins" in Formulation and Process Development Strategies for Manufacturing Biopharmaceuticals, eds. Jameel and Hershenson, John Wiley & Sons, Inc., (2010).
Wang et al., "Antibody Structure, Instability, and Formulation", J. Pharma. Sci., 96 :1-26, (2007).
Wang et al. "Parenteral Formulations of Proteins and Peptides: Satbility and Stabilizers", J. Parenteral Sci. and Tech., 42(2upplS):S3-S26, (1998).
Nelson et al, "Development trends for human monoclonal antibody therapeutics", Nature Reviews, 9 :767-74, (2010).
Liu et al., "Heterogeneity of Monoclonal Antibodies", J. Pharma. Sci. 97 :2426-2447, (2008).
Singh et al., "Best Practices for the Formulation and Manufacturing of Biotech Drug Products", Biopharm Intl., pp. 32-48, (2009).
McGoff P, Scher DS., "Solution formulation of proteins/peptides" In: McNally EJ, editor. Protein Formulation and Delivery. New York, NY: Marcel Dekker; (2000), pp. 139-158.
Shire, Steve, "Formulation and manufacturability of biologics", Current Opinion Biotech, 20:1-7, (2009).
European Medicines Agency, "CHMP Assessment Report for Ilaris", retrieved from www.ema.europa.eu/docs/en_GB/document_library/EPAR_-_Public_assessment_report/human/001109/WC500031679.pdf on Jan. 18, 2012.
Office Action from Corresponding Chinese Patent Application No. CN 200980149644.4, issued on Oct. 21, 2013.

* cited by examiner

Primary Examiner — David Romeo
(74) Attorney, Agent, or Firm — Leslie Fischer (57) ABSTRACT The present invention relates to novel pharmaceutical formulations, in particular novel pharmaceutical formulations in which the active ingredient comprises human antibodies to human interleukin I beta (IL-1β), in particular ACZ885 antibody, pharmaceutical formulations which are stable and aggregate-free upon storage and delivery.

9 Claims, 2 Drawing Sheets

SEQUENCE LISTING

<160> NUMBER OF SEQ ID NOS: 4

<210> SEQ ID NO 1
<211> LENGTH: 137
<212> TYPE: PRT
<213> ORGANISM: Human

<400> SEQUENCE: 1

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser
    130                 135

<210> SEQ ID NO 2
<211> LENGTH: 126
<212> TYPE: PRT
<213> ORGANISM: Human

<400> SEQUENCE: 2

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys
        115                 120                 125

```
<210> SEQ ID NO 3
<211> LENGTH: 410
<212> TYPE: DNA
<213> ORGANISM: human

<400> SEQUENCE: 3
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtgtt tatggcatga actgggtccg ccaggctcca     180
ggcaaggggc tggagtgggt ggcaattatt tggtatgatg agataatca atactatgca      240 gactccgtga agggccgatt caccatctcc agagacaatt ccaagaacac gctgtatctg     300
caaatgaacg gcctgagagc cgaggacacg gctgtgtatt attgtgcgag agatcttagg     360
actgggcctt ttgactactg gggccaggga accctggtca ccgtctcctc              410

<210> SEQ ID NO 4
<211> LENGTH: 378
<212> TYPE: DNA
<213> ORGANISM: human

<400> SEQUENCE: 4
atgttgccat cacaactcat tgggtttctg ctgctctggg ttccagcctc caggggtgaa      60
attgtgctga ctcagtctcc agactttcag tctgtgactc caaaggagaa agtcaccatc     120
acctgccggg ccagtcagag cattggtagt agcttacact ggtaccagca gaaaccagat     180
cagtctccaa agctcctcat caagtatgct tcccagtcct ctcagggggt cccctcgagg     240
ttcagtggca gtggatctgg gacagatttc accctcacca tcaatagcct ggaagctgaa     300
gatgctgcag cgtattactg tcatcagagt agtagtttac cattcacttt cggccctggg     360
accaaagtgg atatcaaa                                                  378
```

ANTIBODY FORMULATION

The instant application is a continuation of U.S. patent application Ser. No. 13/133,843, filed Jun. 9, 2011, which is a National Phase entry (371) of International Patent Application No. PCT/EP09/066675, filed Dec. 9, 2009, which claims priority to European Patent Application No. 08170884.4, filed Dec. 10, 2008, the contents of which are hereby incorporated by reference herein in their entirety.

The present invention relates to novel pharmaceutical formulations, in particular novel pharmaceutical formulations in which the active ingredient comprises human antibodies to human interleukin I beta (IL-1β), in particular antibodies described in WO 2002/016436.

Antibodies, as other protein therapeutics are complex molecules and in general, large amounts of antibodies have to be used in pharmaceutical formulations due to their therapeutically effective dose in mammals, particularly humans. Liquid formulations of protein therapeutics should preserve intact the biologic activity of the protein therapeutics and protect the functional groups of the protein therapeutics from degradation during manufacturing and shelf life. Degradation pathways for proteins can involve chemical instability or physical instability.

Early suggestions about how to solve the problems of instability of protein therapeutics formulations included the lyophilization of the drug product, followed by reconstitution immediately or shortly prior to administration. However, the reconstituted formulation requires being reproducible, stable and physiologically active in order to achieve a safe preparation with effective therapeutic results.

Conveniently, liquid pharmaceutical formulations of protein therapeutics, i.e. antibodies should be long-term stable, contain a safe and effective amount of the pharmaceutical compound.

A long appreciated problem with liquid formulations of protein therapeutics is that of aggregation, where protein molecules physically stick together, for example, resulting in the formation of opaque insoluble matter or precipitation, which may show undesired immunological reactions. Additionally, a major problem caused by the aggregate formation is that during the administration the formulation may block syringes or pumps and rendering it unsafe to patients.

Thus, there is a need for formulations comprising protein therapeutics, in particular antibodies that are long-term stable, free of aggregation at high antibody concentrations. The present invention addresses the above-identified need by providing a novel formulation comprising an antibody, free of protein aggregates, stable and having sufficiently low viscosity and which is therefore suitable for administration to mammalians, particularly human subjects.

Interleukin-1β (IL-1 beta or IL-1β or Interleukin-1β have the same meaning herein) is a potent immuno-modulator which mediates a wide range of immune and inflammatory responses.

Inappropriate or excessive production of 1β is associated with the pathology of various diseases and disorders, such as septicemia, septic or endotoxic shock, allergies, asthma, bone loss, ischemia, stroke, rheumatoid arthritis and other inflammatory disorders. Antibodies to IL-1β have been proposed for use in the treatment of IL-1 mediated diseases and disorders; see for instance, WO 95/01997 and the discussion in the introduction thereof and WO 02/16436, the content of which is incorporated by reference.

Particularly preferred antibody to IL-1β for the formulations of the present invention is the ACZ885 antibody as hereinafter described in SEQ ID NO:1 and SEQ ID NO:2, or functional fragments thereof retaining affinity for the antigen, such as F(ab)2, Fab, scFv, VH domains, CDR's. The mature ACZ885 antibody comprises the heavy chain amino acid sequence as set forth in SEQ ID NO:1 less the 19-amino acid leader sequence (i.e., the mature ACZ885 antibody comprises the variably heavy chain set forth as amino acids 20 to 137 of SEQ ID NO:1) and the light chain amino acid sequence as set forth in SEQ ID NO:2 less the 19-amino acid leader sequence (i.e., the mature ACZ885 antibody comprises the variably heavy chain set forth as amino acids 20 to 126 of SEQ ID NO:2). ACZ885 is a human IgG$_1$/k antibody.

It is an object of the present invention to provide an antibody formulation which is stable upon storage and delivery. According to the present invention a stable formulation is a formulation wherein the antibody therein essentially retains its physical and chemical stability and integrity upon storage. For example, the extent of product related substances and impurities following lyophilization and storage or storage in the case of liquid formulation is about 2-5%, preferably 2-3%. The stability of the antibody formulation may be measured using biological activity assays and wherein the biological activity upon storage is of about 80-125% of the original activity. The biological activity of the antibody in the formulation of the invention upon storage is measured in a reporter gene assay, using the genetically modified cell line as described in the examples section hereinafter.

It is a further object to provide a stable liquid antibody formulation which is suitable for subcutaneous administration. Preferably the liquid formulation is also suitable for lyophilisation and subsequent reconstitution. It is also an object to provide a formulation which is stable for at least the time over which it will be administered to a mammalian, in particular human subject.

In general, it is preferred to use small volumes of pharmaceutical formulation for subcutaneous injection (usually 1.0 mL-1.2 mL at a maximum). In the case of formulations comprising antibodies, e.g. high dose antibody therapies, the subcutaneous administration requires high concentration antibody formulations (e.g., 50 mg/ml -150 mg/ml or more).

Because of the required high antibody concentrations, the formulations comprising antibodies pose challenges relating to the physical and chemical stability of the antibody, formation of aggregates and difficulty with manufacture, storage, and delivery of the antibody formulation.

Increased viscosity of protein formulations has negative implications from processing, e.g. processability of the liquid through drug delivery to the patient, e.g. at high viscosity, the liquid formulation do not longer pass through the gauge of a needle without difficulty, causing discomfort to the patient; injection duration; utilizability of auto-injector. Additionally relatively high concentration antibody formulations with suitably low viscosities are desired as a prerequisite for easy manufacturing, storage, and administration. The term "viscosity" as used herein, may be "kinematic viscosity" or "absolute viscosity." Commonly, kinematic viscosity is expressed in centistokes (cSt). The SI unit of kinematic viscosity is mm 2/s, which is 1 cSt. Absolute viscosity is expressed in units of centipoise (cP). The SI unit of absolute viscosity is the millipascal-second (mPa-s), where 1 cP=1 mPa-s.

Therefore the present invention provides formulations comprising IL-1β antibodies and which are stable and aggregate-free at high antibody concentrations while having a sufficiently low viscosity.

A liquid pharmaceutical antibody formulation should exhibit a variety of pre-defined characteristics. One of the major concerns in liquid drug products is stability, as proteins tend to form soluble and insoluble aggregates during manufacturing and storage. In addition, various chemical reactions can occur in solution (deamidation, oxidation, clipping, isomerization etc.) leading to an increase in degradation product levels and/or loss of bioactivity. Preferably, a liquid antibody formulation should exhibit a shelf life of more than 18 months Most preferred a liquid ACZ885 formulation should exhibit a shelf life of more than 24 months. The shelf life and activity of an IL-1β antibody is defined in the bioactivity assay in the examples section, whereby the activity should remain between 80% and 125% of the original activity.

An antibody formulation, in particular ACZ885 antibody formulation should exhibit a shelf life of about 36 to 60 months at 2-8° C. Preferably, the ACZ885 liquid formulation should exhibit a shelf life of about 24 to 36 months at 2-8° C. Preferably, the ACZ885 loyphilizate formulation should exhibit a shelf life of about preferably up to 60 months at 2-8° C.

The main factors determining shelf life usually are formation of by - and degradation products and loss of bioactivity. The formulation of the current invention achieves these desired stability levels.

Apart from sufficient physical and chemical stability the formulation should be of acceptable pH value and osmolality (250 to 500 mOsm/kg) for subcutaneous application. However it was reported in literature that preparations with high osmolality (up to 1100 mOsm/kg) could be administered subcutaneously without significantly increased pain perception or burning duration after injection. It is also known that high concentration of antibodies would increase the viscosity of the formulation and also the aggregation. Suitable pharmaceutical formulation according to the invention have a viscosity of about less than 16 mPas, preferably 3 to 16 mPas, and preferred 3-10 mPas.

In accordance with the present invention it has now surprisingly been found that particularly stable antibody formulations are obtainable that have advantageous properties in preserving antibody activity of long period of storage, avoiding aggregation and having a suitable viscosity despite high antibody concentrations. The present invention provides in its broadest aspect a pharmaceutical formulation (formulation of the invention) comprising an antibody, as active ingredient and a buffer system, a stabilizer and a surfactant. The formulation of the invention is liquid but is also suitable to be lyophilized and subsequently be reconstituted to a liquid formulation with a lower, same or higher antibody concentration. A reconstituted formulation is a formulation which has been prepared from a lyophilizate, such that the antibody of the formulation is dispersed in the reconstituted formulation The present invention relates to novel formulation comprising antibodies to IL-1β, as active ingredient and a buffer system, wherein the pH value is from 5.5 to 7.5, preferably from 5.5 to 7, preferred from 6.2 to 6.8. More specifically, the invention relates to novel pharmaceutical formulation comprising ACZ885 antibody, as active ingredient and a buffer system, wherein the pH value is from 5.5 to 7.5, preferably from 5.5 to 7, preferred from 6.2 to 6.8.

We have now discovered that a stable formulation can be prepared using a buffer system resulting in a formulation having a pH of from 5.5 to 7.5, preferably from 5.5 to 7, preferred from 6.2 to 6.8. In a particular aspect, the pH is any pH value within those enumerated above; for example 6.2, 6.3, 6.4, 6.5, 6.6, 6.7, 6.8.

Preferred buffer systems according to the present invention include citrate, histidine, sodium succinate, and sodium and/or potassium phosphate buffer systems, and other organic acids or inorganic acids, more preferably, histidine or citrate, and best results were obtained using histidine.

The concentration of the suitable buffer system used for the formulation according to the present invention is from about 10 mM to about 50 mM, or from about 10 mM to about 40 mM, depending, for example, on the buffer and the desired stability of the formulation.

In the preferred embodiment, the buffer system is histidine; and histidine is preferably used at a concentration from 10 to 50 mM, preferably from 15 to 40 mM, preferred from 20 to 30 mM.

The formulation of the invention may preferably further comprise a stabilizer. Stabilizers according to the present invention include sucrose, trehalose, mannitol, sorbitol and arginine hydrochloride. Best results are obtained when sucrose or mannitol is used. The concentration of the suitable stabilizers used for the formulation according to the present invention is from about 50 to 300 mM, preferably from 180 to 300 mM, most preferred about 270 mM of sucrose or mannitol. In a particular aspect the lyophilized and reconstituted liquid formulation comprises sucrose or mannitol as stabilizer. In another particular aspect, the liquid formulation comprises mannitol as stabilizer.

The formulation of the invention may optionally further comprise one or more excipients selected from a group comprising bulking agent, salt, surfactant and preservative.

A bulking agent is a compound which adds mass to a pharmaceutical formulation and contributes to the physical structure of the formulation in lyophilized form. Suitable bulking agents according to the present invention include mannitol, glycine, polyethylene glycol and sorbitol. The concentration of the bulking agent used for the formulation according to the present invention is 20-90 mM.

The use of a surfactant can reduce aggregation of the reconstituted protein and/or reduce the formation of particulates in the reconstituted formulation. The amount of surfactant added is such that it reduces aggregation of the reconstituted protein and minimizes the formation of particulates after reconstitution.

Suitable surfactants according to the present invention include polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl-or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT® series (Mona Industries, Inc., Paterson, N.J.), polyethyl glycol, polypropyl glycol, and copolymers of ethylene and propylene glycol (e.g. Pluronics, PF68 etc). In a preferred embodiment, the surfactant may be selected from the group consisting of polysorbates 20 and polysorbates 80, The concentration of the surfactant used for the formulation according to the present invention is from about 0.001-0.5%, or from about 0.005-0.10%, preferably 0.01 to 0.10%, most preferred from about 0.04 to 0.06% weight by volume of the formulation. The surfactant can be added to the pre-lyophilized formulation, the lyophilized formulation and/or the reconstituted formulation as desired, but preferably the pre-lyophilized formulation.

Optionally preservatives may be used in formulations of invention. Suitable preservatives for use in the formulation of the invention include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

Other pharmaceutically acceptable carriers, excipients or stabilizers such as those described in Remington's Science and Practice of Pharmacy 21st edition, (2005) or Art, Science and Technology of Pharmaceutical Compounding, $3^{rd}$ edition (2008) may be included in the formulation of the invention provided that they do not adversely affect the desired characteristics of the formulation. Acceptable carriers, excipients or stabilizers are nontoxic to recipients at the dosages and concentrations employed and include additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The invention provides, in one aspect a stable liquid, lyophilized or reconstituted formulation comprising an antibody, preferably an antibody to IL-1β, most preferred ACZ885 and a buffer system, wherein the pH of the liquid or reconstituted formulation is from 5.5 to 7.5, preferably from 5.5 to 7, preferred from 6.2 to 6.8 in order to achieve sufficient stability, minimal aggregation and acceptably low viscosity. The formulation according to the present invention is suitable for lyophilization and the reconstitution with water is achieved within acceptable period of time, typically less than 10 minutes. The invention provides a stable reconstituted formulation comprising an antibody to IL-1β, most preferred ACZ885 antibody, and a buffer system, which reconstituted formulation has been prepared from a lyophilized mixture of the antibody, and a buffer system, wherein the pH of the reconstituted formulation is from 5.5 to 7.5, preferably from 5.5 to 7, preferred from 6.2 to 6.8., and reconstitution time is below 10 mins. A stable reconstituted formulation is a formulation wherein the antibody therein essentially retains its physical and chemical stability and integrity upon storage for a period of time from the reconstitution to the use, typically a few hours and up to several days. In a further embodiment, the invention provides a method for preparing a formulation comprising the steps of: (a) lyophilizing the formulation comprising the antibody to IL-1β, most preferred ACZ885 antibody, and a buffer system; and (b) reconstituting the lyophilized mixture of step (a) in a reconstitution medium such that the reconstituted formulation is stable.

The formulation of step (a) may further comprise a stabilizer and one or more excipients selected from a group comprising bulking agent, salt, surfactant and preservative as hereinabove described.

As reconstitution media several diluted organic acids or water, i.e. sterile water, bacteriostatic water for injection (BWFI) or may be used. The reconstitution medium may be selected from water, i.e. sterile water, bacteriostatic water for injection (BWFI) or the group consisting of acetic acid, propionic acid, succinic acid, sodium chloride, magnesium chloride, acidic solution of sodium chloride, acidic solution of magnesium chloride and acidic solution of arginine, in an amount from about 50 to about 100 mM.

The invention thus provides pharmaceutical formulation comprising:
a) an antibody to IL-1β, preferably ACZ885 antibody; used in a concentration of about 10 to 150 mg/ml; and b) a buffer system, preferably citrate, histidine, sodium succinate, or sodium and/or potassium phosphate buffer systems, most preferred histidine buffer system and the buffer system may be used in a concentration of about 10 to 50 mM; and wherein the pH of the buffer system is any pH value within 5.5 to 7.5, preferably 6.2 to 6.8; and optionally:

c) a stabilizer, preferably sucrose, trehalose, mannitol, sorbitol or arginine hydrochloride, most preferred sucrose or mannitol at a concentration of about 50 to 300 mM; and optionally d) further excipients selected from the group comprising bulking agent, salt, surfactant and preservative.

In certain embodiments of the invention, a bulking agent (e.g. mannitol or glycine) is used in the preparation of the pre-lyophilization formulation. The bulking agent may allow for the production of a uniform lyophilized cake without excessive pockets therein.

A preferred liquid formulation of the present invention provides a formulation comprising ACZ885 at concentration: 10-150 mg/ml, 270 mM mannitol, 20 mM histidine and 0.04% polysorbate 80, wherein the pH of the formulation is 6.5.

A preferred reconstituted formulation of the invention provides a lyophilisate which in reconstituted form yields a reconstituted formulation comprising ACZ885 at concentration: 10-150 mg/ml, 270 mM sucrose, 30 mM histidine and 0.06% polysorbate 80, wherein the pH of the formulation is 6.5.

The invention further provides a method for treating a mammal, particularly human subject comprising administering a therapeutically effective amount of a reconstituted formulation disclosed herein to a mammal, particularly human subject wherein the mammal, particularly human subject has a disorder requiring treatment with antibody to IL-1β, most preferred ACZ885. For example, the formulation may be administered subcutaneously.

Formulations of the invention are useful for the prophylaxis and treatment of IL-1 mediated diseases or medical conditions, e.g. inflammatory conditions, allergies and allergic conditions, hypersensitivity reactions, autoimmune diseases, severe infections, and organ or tissue transplant rejection.

It is an object of the present invention to provide a use of the formulation of the invention for the treatment of IL-1 mediated diseases or medical conditions.

For example, formulations of the invention may be use for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

Formulations of the invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, hypersensitivity (including both airways hypersensitivity and dermal hypersensitivity) and allergies. Specific autoimmune diseases for which formulations of the invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Formulations of the invention are also useful for the treatment, prevention, or amelioration of asthma, bronchitis, pneumoconiosis, pulmonary emphysema, and other obstructive or inflammatory diseases of the airways Formulations of the invention are useful for treating undesirable acute and hyperacute inflammatory reactions which are mediated by IL-1 or involve IL-1 production, especially IL-1, or the promotion of TNF release by IL-1, e.g. acute infections, for example septic shock (e.g., endotoxic shock and adult respiratory distress syndrome), meningitis, pneumonia; and for the treatment of cachexia or wasting syndrome associated with morbid TNF release, consequent to infection, cancer, or organ dysfunction, especially AIDS-related cachexia, e.g., associated with or consequential to HW infection.

Formulations of the invention are particularly useful for treating diseases of bone metabolism including osteoarthritis, osteoporosis and other inflammatory arthritides, and bone loss in general, including age-related bone loss, and in particular periodontal disease.

Formulations of the invention are useful in the prevention and treatment of Auto-Inflammatory Syndromes in patients such as in mammals, particularly humans. Auto-Inflammatory Syndromes according to the inventions are e.g., but not limited to, a group of inherited disorders characterized by recurrent episodes of inflammation, that in contrast to the auto-immune diseases lack high-titer autoantibodies or antigen specific T cells. Furthermore, Auto-inflammatory Syndromes according to the inventions show increased IL-1 beta secretion (loss of negative regulatory role of pyrin which seems mutated in said diseases), NFkB activation and impaired leukocyte apoptosis). Auto-inflammatory Syndromes according to the inventions are Muckle-Wells syndromes (MWS), LADA (Latent Autoimmune Diabetes in Adults), familial cold autoinflammmatory syndrome (FCAS), Cryopyrin-associated periodic syndromes (CAPS), neonatal-onset multisystem inflammatory syndrome (NOMID), chronic infantile neurological, cutaneous, articular (CINCA) syndrome, familial Mediterranean fever (FMF) and/or certain form of juvenile arthritis such as systemic onset juvenile idiopathic arthritis (SJIA), certain form of juvenile rheumatoid arthritis such as systemic onset juvenile idiopathic rheumatoid arthritis and/or certain form of adult rheumatoid arthritis.

Preferably the formulations of the invention are useful in the prevention and treatment of Juvenile rheumatoid arthritis and adult rheumatoid arthritis and/or Muckle Wells Syndrome.

The formulations of the invention may also be useful in the treatment of type 2 diabetes, where clinical and preclinical studies show improved islet function by IL-1 blockade.

Formulations of the invention are also be useful in the treatment of various diabetes related pathologies such as retinopathy, wound healing, vascular diseases, (incl. arterial restenosis after stenting or angioplasty), renal dysfunction, chronic kidney disease and metabolic syndrome and obesity. The formulations of the invention may also be useful in the treatment of migraine, synovitis, gout, pseudogout/gouty arthritis or chondrocalcinosis, chronic obstructive pulmonary disease (COPD), ventilation induced lung damage, various pain conditions, such as morphine resistant pain, neuropathic pain, pre-term birth pain, discogenic pain, inflammatory pain, headache, or migraine. IL-1 beta is involved in pain perception and amplifies neurogenic signals. Furthermore formulations of the invention of the invention are useful in the treatment of atherosclerosis, acute renal colic, biliary colic and pain related to these disorders.

The formulations of the invention may be useful in the treatment of Periodic Fever Syndromes: Familial Mediterranean Fever (FMF), Tumor Necrosis Factor Receptor Associated Periodic Syndrome (TRAPS), Hyperimmunoglobulin D syndrome (HIDS), also called Mevalonate Kinase Associated Periodic Fever Syndrome, Familial Cold auto inflammatory syndrome and Periodic fever, Aphthous-stomatitis, Pharyngitis, Adenitis (PFAPA) Syndrome, where IL-1 beta is a dominant cytokine. Other diseases wherein IL-1 beta is a dominant cytokine and that can be treated with formulations of the invention according to the invention comprise Anti-synthetase syndrome, Macrophage activation syndrome MAS, Behcet Disease, Blau's syndrome, PAPA syndrome, Schnizler's syndrome, Sweet's syndrome. IL-1 beta ligand-receptor blocking and IL-1 beta compounds of the invention may also be used to treat Vasculitides; Giant-cell arteritis (GCA), Henoch-Schoenlein purpura, Primary systemic vasculitis, Kawasaki disease (mucocutaneous lymph node syndrome), Takayasu arteritis, Polyarteritis nodosa, Essential cryoglobulinemic vasculitis, microscopic polyangiitis (MPA) and Churg-Strauss syndrome (CSS), urticarial vasculitis. Furthermore formulations of the invention are useful in the treatment of autoimmune diseases like sarcoidosis, pemphygus, ankylosing spondylitis, Alzheimer disease, amyloidosis, secondary amyloidosis and adult onset Still disease (AOSD).

Formulations of the invention may be used to treat HLA-B27 associated diseases such as but not limited to psoriatica, spondylitis ankylosans, Morbus Reiter and enteropathic arthritis. IL-1 beta compounds according to the invention may be used to treat rheumatic fever, polymyalgia rheumatica and giant cell arthritis. Finally formulations of the invention may be used to treat infections, in particular bacterial infections and viral infections, more in particular bacterial infections associated with arthritic symptoms or observations, such as but not limited to hematogenic osteomyelitis, infectious arthritis, tuberculotic arthritis.

For the above indications, the appropriate dosage will vary depending upon, for example, the particular antibody to IL-1β to be employed, the host, the mode of administration and the nature and severity of the condition being treated. The frequency of dosing for prophylactic uses will normally be in the range from about once per week up to about once every 3 months, more usually in the range from about once every 2 weeks up to about once every 10 weeks, e.g. once every 4 to 8 weeks.

The formulation of the invention is suitably administered to the patient at one time or over a series of treatments and may be administered to the patient at any time from diagnosis onwards; it may be administered as the sole treatment or in conjunction with other drugs or therapies useful in treating the conditions as described herein before.

A prophylactic treatment typically comprises administering the formulation of the invention once per month to once every 2 to 3 months, or less frequently.

The formulation of the invention comprising ACZ885 is administered preferably by intravenous route, but also by subcutaneous or intramuscular injection route. For such purposes, the formulation may be injected using a syringe. For example, the formulation comprising ACZ885 is administered using autoinjector, normal syringe that may be prefilled, optionally in a sterile package, optionally syringes with safety devices. Micro-needle and coated patches with reservoirs are also envisaged as suitable administration devices.

The formulation of the invention may be administered to a mammal, preferably a human in need of treatment with antibody to IL-1β, i.e. ACZ885, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for antibody, at about 120° C. for about 30 minutes, for example.

The formulation of the invention comprising ACZ885 is preferably administered by subcutaneous injection in treatments of rheumatoid arthritis in adults (RA), juvenile RA (SJIA, pJIA), chronic obstructive pulmonary disease (COPD), CAPS, Muckle-Wells syndrome (MWS), Osteoarthritis (OA) and potentially type 2 diabetes and gout.

The present invention further provides an isotonic liquid formulation, which is obtained by dilution of the reconstituted formulation with an infusion solution.

The term treatment refers to both therapeutic treatment and prophylactic or preventative measures.

The term mammal for purposes of treatment refers to any animal classified as a mammal, including humans, domestic and farm animals, and zoo, sports, or pet animals, such as dogs, horses, cats, cows, etc. Preferably, the mammal is human.

A disorder is any condition that would benefit from treatment with an antibody to IL-1β. This includes chronic and acute disorders or diseases including those pathological conditions which predispose the mammal to the disorder in question. Non-limiting examples of disorders to be treated herein include the above-mentioned diseases and disorders.

A therapeutically effective amount is at least the minimum concentration required to effect a measurable improvement or prevention of a particular disorder.

Figure Legends

EXAMPLES

Preparation of a Liquid Formulation and its Lyophilisate

An ACZ885 formulation is developed that allows for both intravenous administration after reconstitution and subsequent dilution and subcutaneous administration after reconstitution.

Four different buffer systems (citrate, histidine, sodium succinate, and sodium/potassium phosphate buffer systems, concentration 40 mM each) were selected to test their suitability for ACZ885 formulations.

Shaking and freeze thaw cycles are used as stress tests to rank order suitability buffer systems with regard to protein aggregation.

Protein aggregation could most efficiently be avoided using histidine or citrate buffer at a pH range of 5.0-7, as shown in the table 1.

TABLE 1

Analytical results of buffer system screening

| Buffer salt | pKa values | pH (planned) | pH (measured) | Sum of Aggregates by SEC [%] |
|---|---|---|---|---|
| Histidine | $pK_a = 6.1$, imidazole group | 6.0 | 5.8 | 0.37 |
| | | 6.5 | 6.2 | 0.21 |
| | | 7.0 | 6.6 | 0.38 |
| Succinate | $pK_{a1} = 4.19$, $pK_{a2} = 5.57$ | 5.0 | 5.2 | 0.39 |
| | | 5.5 | 5.6 | 0.39 |
| | | 6.0 | 6.0 | 0.42 |
| Phosphate | $pK_{a2} = 7.21$ | 6.0 | 6.2 | 0.47 |
| | | 6.5 | 6.7 | 0.74 |
| | | 7.0 | 7.0 | 3.94 |
| Citrate | $pK_{a2} = 4.76$, $pK_{a3} = 6.40$ | 5.0 | 5.3 | 0.38 |
| | | 5.5 | 5.7 | 0.40 |
| | | 6.0 | 6.2 | 0.39 |

Figure 1:
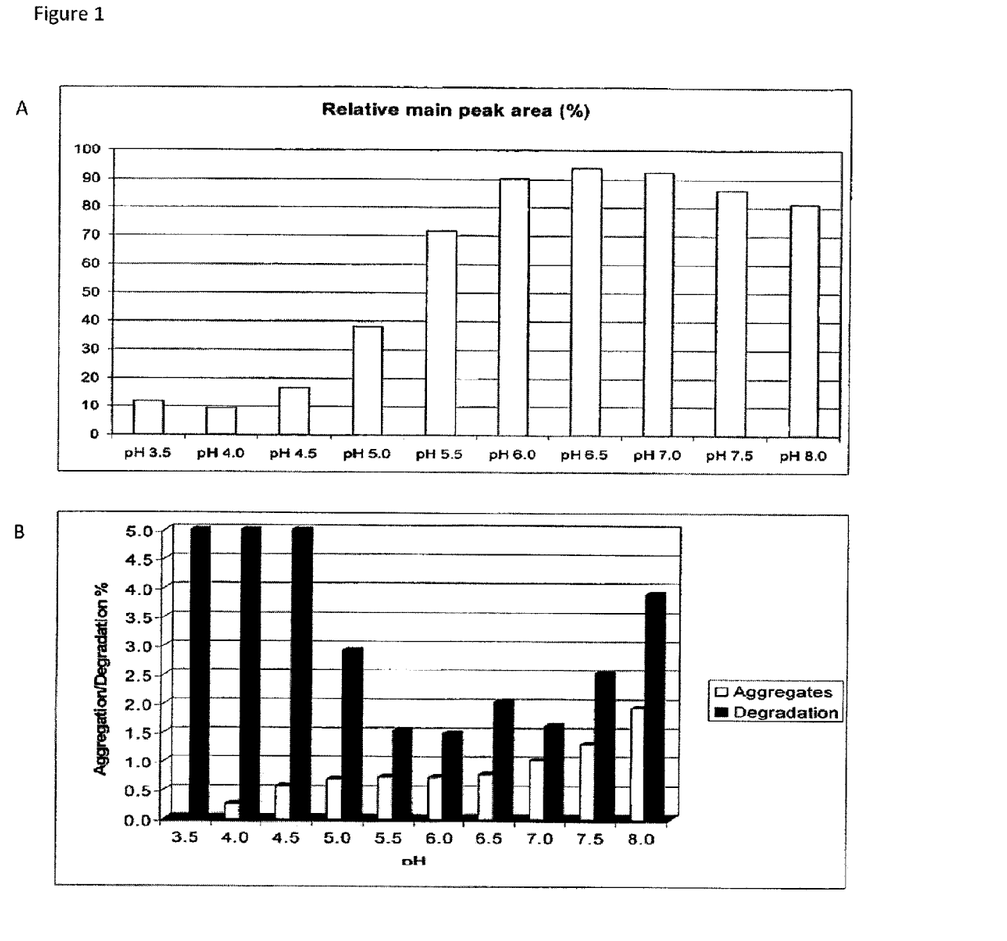
FIG. 1 shows an overview of the results obtained by RP-HPLC (top FIG. 1A) and SEC (bottom FIG. 1B) for ACZ885 formulation after 4 week storage at 40° C.
Figure 2:
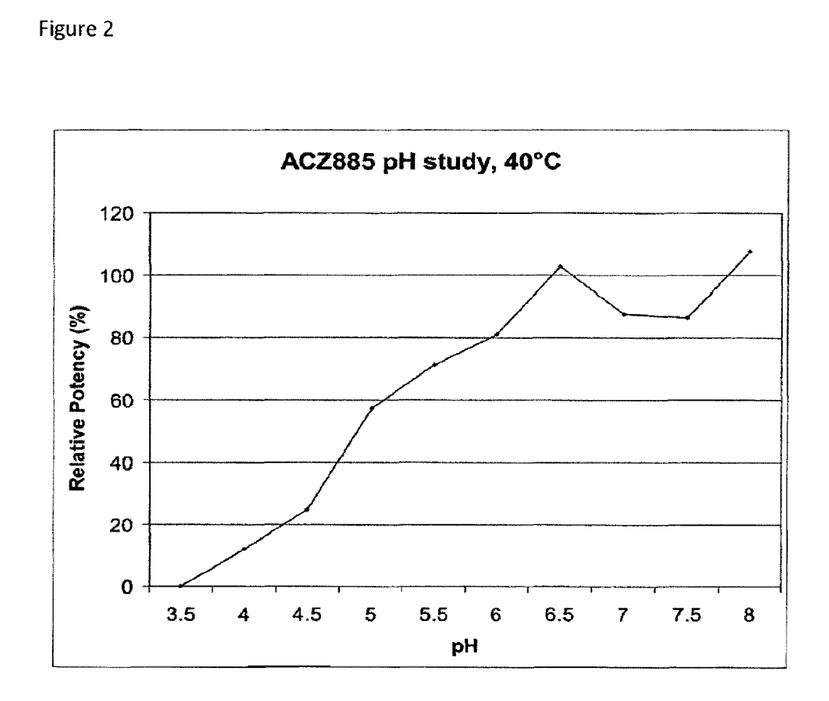
FIG. 2 shows an overview of the results obtained for the relative potency for ACZ885 formulation after 4 week storage at 40° C.

A pH range of 3.5 to 8.0 with increasing steps of 0.5 units was investigated. After 4 week storage at 40° C. different pH optima of 6.2 to 6.8 were concluded based on the results from different analytical techniques applied, as shown in FIG. 1.

TABLE 2

Analytical results for lyophilisation

| Code | Buffer (20 mM) | Sucrose added | Viscosity [mPas] | Osmolarity [mOsm] | Sum of Aggregates by SEC [%] |
|---|---|---|---|---|---|
| F1 | Histidine pH 6.2 | — | 14.8 | 382 | 5.4 |
| F2 | Histidine pH 6.2 | 90 mM | 11.0 | 392 | 0.6 |
| F3 | Citrate pH 6.0 | — | 13.2 | 386 | 3.9 |
| F4 | Citrate pH 6.0 | 90 mM | 11.0 | 445 | 0.6 |

The results for histidine and the citrate buffered samples were similar. Citrate buffer can be critical in subcutaneous formulations due to increased pain perception after application; therefore histidine may be preferred over citrate for subcutaneous applications.

After selection of suitable buffer systems, the impact of stablilizers on protein aggregation was investigated. Formulations containing sucrose, glycine, mannitol, sorbitol or trehalose were analyzed after 6 and 16 weeks storage at 5° C. and 40° C. A yellow coloration was observed for sucrose containing formulations stored at 40° C., probably due to Maillard reaction between amino groups of protein or histidine and the reducing sugar. Sucrose or mannitol containing formulation were selected for lyophilizate and reconstituted formulation.

The formulations containing mannitol were selected for the liquid formulation.

Further studies were performed to assess the influence of surfactant concentration on the physico-chemical stability of the formulation of the invention. The particulate matter data below showed the highest values for the surfactant free formulation, indicating that Tween is beneficial for physical stability of the samples. At a concentration of 0.10% Tween, particulate matter data tend to be higher compared to the lower levels.

TABLE 3

Analytical results for Tween: Subvisible Particles by Light Obscuration (particulate matter) after 10 months

| | 5° C. | | | 25° C. | | |
|---|---|---|---|---|---|---|
| Concentration Tween | Particles/mL > 1.0 μm | Particles/mL > 1.0 μm | Particles/mL > 10.9 μm | Particles/mL > 25.7 μm | Particles/mL > 10.9 μm | Particles/mL > 25.7 μm |
| no Tween | 6353 | 11644 | 14 | 0 | 3 | 0 |
| 0.01% Tween 80 | 862 | 2044 | 0 | 0 | 2 | 0 |
| 0.04% Tween 80 | 1217 | 2077 | 2 | 0 | 0 | 0 |
| 0.10% Tween 80 | 2180 | 2424 | 0 | 0 | 3 | 0 |
| 0.01% Tween 20 | 1349 | 2105 | 0 | 0 | 0 | 0 |
| 0.04% Tween 20 | 1410 | 1077 | 1 | 0 | 2 | 0 |
| 0.10% Tween 20 | 1071 | 2382 | 2 | 0 | 2 | 0 |

Samples of liquid formulation containing 150 mg/mL ACZ885, 20 mM Histidine, 270 mM Mannitol, 0.04% (m/v) Tween 80, having a pH 6.5 were stored at 5° C., 25° C. and 40° C. for up to 24 months. At 5° C., no major amounts of both soluble and insoluble aggregates could be detected. Bioactivity, determined using the reporter gene assay as hereinafter described, was within 70-125%. These data (see Tables 4 to 6) showed that the formulation tested was stable upon storage for 24 months.

TABLE 4

Analytical Data of Screen, 5° C.

| | Storage periods | | | | | |
|---|---|---|---|---|---|---|
| | Start | 2 months | 4 months | 10 months | 16.5 months | 24 months |
| Assay by SEC [mg/mL] | 152.2 | 155.0 | 151.9 | 153.0 | 153.0 | 151.9 |
| Reporter Gene Assay [%] | 121 | n.d. | 97 | 99 | 110 | 99 (n = 4) |
| Appearance of the solution: color | Colorless | Colorless | Slightly brownish (B8-B9) | Slightly brownish (B8-B9) | Slightly brownish (B8) | Brownish (B5-B6) No particles visible |
| Turbidity | n.d. | n.d. | n.d. | n.d. | strongly opalescent (23 NTU) | opalescent (17 NTU) |
| LLS [Da] | 155'750 | 151'800 | 147'400 | 142'300 | 147'800 | 155'700 |
| pH value | 6.7 | 6.7 | 6.6 | 6.6 | 6.6 | 6.6 |
| By- and de-gradation products by SEC [%] | AP1: 0.3 | AP1: 0.4 | AP1: 0.4 DPx: 1.2 | AP1: 0.6 DPx: not resolved | AP1: 0.6 DPx: not resolved | AP1: 0.8 DPx: 0.2 DP3: 0.2 |
| Impurities by SDS-PAGE [%] | 0.8 | 0.8 | 0.8 | 0.8 | 0.9 | 1.1 |
| Impurities by Bioanalyzer [%] | n.d. | n.d. | n.d. | n.d. | H1: 0.7 M1: 3.1 M2: 0.3 M3: 0.7 L1: 0.0 L2: 0.3 sum: 5.2 | H1: 0.7 M1: 2.1 M2: 0.0 M3: 0.6 L1: 0.0 L2: 0.3 sum: 3.8 |
| CEX [%] | n.d. | n.d. | n.d. | n.d. | 0K: 48.7 1K: 19.6 2K: 15.8 Sum Other: 15.9 | 0K: 43.4 1K: 19.1 2K: 10.5 Sum Other: 27.0 |

APx to DP3: from higher to lower molecular weight; AP1: Dimer, DPx: P100, DP3: P50

TABLE

Error! No text of specified style in document. Analytical Data of Screen, 25° C.

| | Storage periods | | | | | |
|---|---|---|---|---|---|---|
| | Start | 2 months | 4 months | 10 months | 16.5 months | 24 months |
| Assay by SEC [mg/mL] | 152.2 | 146.7 | 145.8 | 149.8 | 141.8 | 134.2 |
| Reporter Gene Assay [%] | 121 | n.d. | 100 | 85 | 74 | 70 (n = 4) |
| Appearance of the solution: color | Colorless | Colorless | Slightly brownish (B8-B9) | Slightly brownish (B8-B9) | Slightly brownish (B6) | Brownish (B5-B6) No particles visible |

TABLE-continued

Analytical Data of Screen, 25° C.

| | Storage periods | | | | | |
|---|---|---|---|---|---|---|
| | Start | 2 months | 4 months | 10 months | 16.5 months | 24 months |
| Turbidity | n.d. | n.d. | n.d. | n.d. | strongly opalescent (22 NTU) | strongly opalescent (24 NTU) |
| LLS [Da] | 155'750 | 150'250 | 152'750 | 148'700 | 172'250 | 189'800 |
| pH value | 6.7 | 6.7 | 6.6 | 6.6 | 6.6 | 6.6 |
| By- and de-gradation products by SEC [%] | — | — | — | — | — | APx: 0.4 |
| | — | — | — | — | — | AP2: 0.2 |
| | AP1: 0.3 | AP1: 0.7 | AP1: 0.9 | AP1: 1.8 | AP1: 2.6 | AP1: 3.7 |
| | — | — | — | AP: 0.2 | AP: 0.2 | AP: 0.5 |
| | — | — | DPx: 1.4 | DPx: 3.7 | DPx: 1.7 | DPx: 2.6 |
| | — | DP3: 0.1 | DP3: 0.2 | DP3: 0.6 | DP3: 1.1 | DP3: 1.5 |
| Impurities by SDS-PAGE [%] | 0.8 | 1.5 | 1.7 | 3.6 | 4.2 | 6.7 |
| Impurities by Bioanalyzer [%] | n.d. | n.d. | n.d. | n.d. | H1: 1.7 | H1: 2.1 |
| | | | | | H2: 0.0 | H2: 0.4 |
| | | | | | H3: 0.0 | H3: 0.3 |
| | | | | | M1: 4.1 | M1: 3.7 |
| | | | | | M2: 1.0 | M2: 1.1 |
| | | | | | M3: 0.7 | M3: 0.7 |
| | | | | | M4: 0.3 | M4: 0.0 |
| | | | | | L1: 0.4 | L1: 0.6 |
| | | | | | L2: 0.8 | L2: 0.7 |
| | | | | | sum: 8.9 | sum: 9.7 |
| CEX [%] | n.d. | n.d. | n.d. | n.d. | 0K: 36.2 | 0K: 12.6 |
| | | | | | 1K: 16.6 | 1K: 6.7 |
| | | | | | 2K: 11.0 | 2K: 3.3 |
| | | | | | Sum Other: 36.2 | Sum Other: 77.4 |

APx to DP3: from higher to lower molecular weight; AP1: Dimer, DPx: P100, DP3: P50

TABLE 1

Analytical Data of Screen, 40° C.

| | Storage periods | | | | |
|---|---|---|---|---|---|
| | Start | 2 months | 4 months | 10 months | 16.5 months |
| Assay by SEC [mg/mL] | 152.2 | 142.9 | 128.1 | 114.1 | 94.5 |
| Reporter Gene Assay [%] | 121 | 78 | 53 | n.d. | n.d. |
| Appearance of the solution: color | Colorless | Slightly brownish (B7) | Slightly brownish (B6-B7) | Yellow (G4-G5) | Brownish (B4) |
| Turbidity | n.d. | n.d. | n.d. | n.d. | out of range (58 NTU) |
| LLS [Da] | 155'750 | 162'950 | 192'500 | 259'650 | 403'350 |
| pH value | 6.7 | 6.6 | 6.6 | 6.6 | 6.6 |
| By- and de-gradation products by SEC [%] | — | APx: 0.4 | APx: 1.9 | APx: 4.4 | APx: 6.1 |
| | — | AP2: 0.1 | AP2: 0.3 | AP2: 1.4 | AP2: 2.1 |
| | AP1: 0.3 | AP1: 2.8 | AP1: 5.0 | AP1: 10.2 | AP1: 15.0 |
| | — | AP: 0.2 | AP: 0.8 | AP: 2.2 | AP: 3.3 |
| | — | — | DPx: 5.5 | DPx: 11.7 | DPx: 12.2 |
| | — | DP3: 0.9 | DP3: 1.9 | DP3: 4.4 | DP3: 8.6 |
| Impurities by SDS-PAGE [%] | 0.8 | 5.8 | 6.7 | 12.5 | 13.3 |
| CEX [%] | n.d. | n.d. | n.d. | n.d. | see chromatogram |

APx to DP3: from higher to lower molecular weight; AP1: Dimer, DPx: P100, DP3: P50

Reconstitution of the Lyophilized Formulation

Liquid formulations for ACZ885 according to the invention are suitable for lyophilization.

Lyophilisation can be done under normal conditions well known in the art of pharmacy. A bulking agent may be included add weight and visibility to the lyophilisate, such as glycine. After the antibody, buffer agent, in an amount from 10 to 40 mM), stabilizer and surfactant are mixed together, the formulation is lyophilized.

TABLE 7

Formulations for technical stability (before lyophilization)

| Code | Sucrose [mM] | Histidine pH 6.0-6.2 [mM] | Tween 80 [%] |
|---|---|---|---|
| F1 | 60 | 10 | 0.02 |
| F3 | 90 | 10 | 0.02 |

Reconstitution generally takes place at a temperature 15-25° C. to ensure complete hydration. The lyophilizate is reconstituted with sterile water.

The target concentration after reconstitution is 150 mg/ml, each formulation being lyophilised and reconstituted with water.

Stability

Different formulations are stored for three months at 2-8° C., 25° C. and 40° C.

The aggregation following lyophilization and storage is used as an indicator of protein stability.

Reporter Gene Assay

The biological activity of ACZ885 was measured in a reporter gene assay, using the genetically modified cell line. This cell line was derived from the human embryonic kidney cell, and was stably transfected with a reporter construct in which the promoter NF-kappa b (an IL-1β-responsive promoter) was fused upstream of the luciferase gene.

Transfection was done by co introduction of a neomycin resistance gene. In this cell line, exposure to IL-1β stimulated the expression of luciferase in a dose-dependent manner.

Addition of graded amounts of ACZ885 to a fixed, submaximal dose of IL-1β caused a decrease in the expression of luciferase during an incubation period up to 18 hours. At the end of the incubation period, the amount of luciferase was quantified based on its enzymatic activity in the cell lysate. Luciferase catalysed the conversion of the substrate luciferin to oxyluciferin, a chemiluminescent product. The resultant glow-type chemiluminescence was then determined with an appropriate luminometer.

The biological potency of an ACZ885 test sample was determined by comparing its ability to inhibit the IL-1β-dependent induction of luciferase activity to that of an ACZ885 reference standard. The samples and standard were normalized on the basis of protein content. Relative potency was then calculated using a parallel line assay according to the European Pharmacopoeia. The final result was expressed as relative potency (in percent) of a sample compared to the reference standard.

Reagents and Buffers:
  Basic medium for cell culture MEM+Earle's+L-Glutamine;
  Fetal calf serum (FCS) heat inactivated, mycoplasma screened;
  Geneticin;
  Cell dissociation buffer enzyme-free, PBS-based;
  Basic medium for assay OptiMEM-I+GlutaMAX-I;
  Luciferase substrate for glow-type chemiluminescence;
  Recombinant Interleukin-1 beta (IL-1β).

Assay Procedure Steps:
(1) Various concentrations of the reference standard and test samples were prepared by performing several 1:2 dilutions from a starting solution of 400 ng/ml ACZ885;
(2) $2\times10^4$ cells resuspended in assay media were added to each well of a 96-well microtiter plate;
(3) The assay was started by the addition of an IL-1 beta solution. Incubation in a humidified $CO_2$ incubator was for up to 18 h;
(4) After the incubation, luciferase substrate solution was added to all wells. The plate was further incubated in the dark for 10 minutes and the luminescence of each well was determined by an appropriate microtiter plate luminescence reader;
(6) The unweighted mean relative potency of a sample was calculated using the parallel line evaluation according to EP from at least two independent experiments.

TABLE 8

Analytical results for the technical stability:

| | Code | Reconstitution time | Opalescence | pH | Assay by UV [mg/ml] | Iso-quant iso-asp/protein [%] | Molecular weight by LLS [kDa] | Sum of Aggregates by SEC [%] | Assay by SEC [mg/ml] | Bioassay [%] |
|---|---|---|---|---|---|---|---|---|---|---|
| F1 | 5° C. (I) | 4 min 45 sec | none | 6.2 | 171.8 | 3.8 | 149.2 | 1.0 | 164.8 | 103 |
| | 5° C. (II) | 4 min 30 sec | none | 6.2 | 172.5 | 3.9 | 149.4 | 1.0 | 167.7 | |
| | 25° C. (I) | 4 min 45 sec | none | 6.2 | 171.9 | 5.6 | 152.7 | 2.7 | 163.6 | 99 |
| | 25° C. (II) | 4 min 45 sec | none | 6.2 | 168.4 | 6.3 | 153.3 | 2.7 | 160.0 | |
| | 40° C. (I) | 4 min 30 sec | none | 6.2 | 172.5 | 9.5 | 161.6 | 7.6 | 152.7 | 93 |
| | 40° C. (II) * | >12 min | none | 6.2 | 166.2 | 10.3 | 162.9 | 7.9 | 153.0 | |
| F3 | 5° C. (I) | 4 min 00 sec | none | 6.2 | 167.4 | 3.4 | 149.6 | 0.8 | 163.1 | 101 |
| | 5° C. (II) | 4 min 00 sec | none | 6.2 | 162.8 | 3.1 | 149.1 | 0.8 | 163.0 | |
| | 25° C. (I) | 4 min 30 sec | none | 6.2 | 159.4 | 4.9 | 151.4 | 1.7 | 158.2 | 91 |
| | 25° C. (II) | 4 min 30 sec | none | 6.2 | 155.1 | 4.7 | 152.3 | 1.6 | 161.7 | |
| | 40° C. (I) * | 4 min 45 sec | none | 6.2 | 164.4 | 6.6 | 156.6 | 4.5 | 154.9 | 95 |
| | 40° C. (II) * | 5 min 45 sec | none | 6.2 | 166.01 | 6.1 | 155.7 | 4.5 | 156.8 | |

* pieces of the cake stick to the bottom.

Formulation 3 showed the lowest amount of aggregation. Formulations 1 and 3 showed a biological activity upon storage of about 90-105% of the original activity.

Administration of the Formulation

The appropriate dosage (i.e. therapeutically effective amount) of ACZ885 depends, for example, on the condition to be treated, the severity and course of the condition, whether ACZ885 is administered for preventive or therapeutic purposes, previous therapy, the patient's clinical history and response to ACZ885, and the discretion of the attending physician.

What is claimed is:

1. A pharmaceutical formulation, comprising 50 to 150 mg/ml of an antibody to IL-1β which comprises amino acids 20 to 137 of SEQ ID NO:1 and amino acids 20 to 126 of SEQ ID NO:2, about 270 mM mannitol, a histidine buffer and about 0.04 to 0.06% polysorbate 80, wherein the pH of the formulation is 5.5 to 7.0, wherein the pharmaceutical formulation is in liquid form, and further wherein the formulation maintains at least about 70% activity following storage for 24 months at 25° C. as determined by a reporter gene assay.

2. The pharmaceutical formulation of claim 1, wherein the pH of the formulation is 6.2 to 6.8.

3. The pharmaceutical formulation of claim 2, wherein the pH of the formulation is 6.5.

4. The pharmaceutical formulation of claim 1, wherein the antibody is ACZ885 and the buffer is 20-30 mM histidine.

5. The pharmaceutical formulation of claim 2, wherein the antibody is ACZ885 and the buffer is 20-30 mM histidine.

6. The pharmaceutical formulation of claim 3, wherein the antibody is ACZ885 and the buffer is 20-30 mM histidine.

7. The pharmaceutical formulation of claim 4, wherein the concentration of the antibody is 150 mg/ml, the concentration of histidine is 20 mM, and the concentration of polysorbate 80 is 0.04% (m/v).

8. The pharmaceutical formulation of claim 5, wherein the concentration of the antibody is 150 mg/ml, the concentration of histidine is 20 mM, and the concentration of polysorbate 80 is 0.04% (m/v).

9. The pharmaceutical formulation of claim 6, wherein the concentration of the antibody is 150 mg/ml, the concentration of histidine is 20 mM, and the concentration of polysorbate 80 is 0.04% (m/v).

* * * * *